(12) United States Patent
Rodriguez Fernandez et al.

(10) Patent No.: US 8,790,245 B2
(45) Date of Patent: Jul. 29, 2014

(54) REMOTE TRACTION AND GUIDANCE SYSTEM FOR MINI-INVASIVE SURGERY

(75) Inventors: Manuel Rodriguez Fernandez, Las Condes (CL); Alberto Rodriguez Navarro, San Francisco, CA (US)

(73) Assignee: Levita Magnetics International Corp., Redwood City, CA (US)

( * ) Notice: Subject to any disclaimer, the term of this patent is extended or adjusted under 35 U.S.C. 154(b) by 19 days.

(21) Appl. No.: 13/132,185

(22) PCT Filed: Oct. 1, 2009

(86) PCT No.: PCT/IB2009/054307
§ 371 (c)(1),
(2), (4) Date: Aug. 17, 2011

(87) PCT Pub. No.: WO2010/089635
PCT Pub. Date: Aug. 12, 2010

(65) Prior Publication Data
US 2011/0295067 A1 Dec. 1, 2011

(30) Foreign Application Priority Data
Feb. 6, 2009 (CL) .................................... 279-2009

(51) Int. Cl.
*A61B 1/00* (2006.01)
(52) U.S. Cl.
USPC .......................................... 600/106; 600/217
(58) Field of Classification Search
USPC ......... 600/106, 107, 217; 606/99, 86 A, 86 B
See application file for complete search history.

(56) References Cited

U.S. PATENT DOCUMENTS

| 2,863,444 A | 12/1958 | Winsten |
| 4,380,999 A | 4/1983 | Healy |
| 5,282,806 A | 2/1994 | Haber et al. |
| 5,415,160 A | 5/1995 | Ortiz et al. |
| 5,449,361 A * | 9/1995 | Preissman ..................... 606/103 |
| 5,458,603 A | 10/1995 | Futch, Sr. |

(Continued)

FOREIGN PATENT DOCUMENTS

| CA | 2 748 471 | 7/2010 |
| CN | 2244381 Y | 11/1996 |

(Continued)

OTHER PUBLICATIONS

International Search Report for International Application No. PCT/IB2009/054307 dated Feb. 8, 2010.

(Continued)

*Primary Examiner* — Eduardo C Robert
*Assistant Examiner* — Julianna N Harvey
(74) *Attorney, Agent, or Firm* — Morrison & Foerster LLP

(57) ABSTRACT

A system for mini-invasive surgery in a body cavity that is easily positioned and hooked including at least one detachable surgical endoclamp (10), assembled with an introduction guide (20) and at an initially open position; and at a naturally closed position when detached from the introduction guide (20) by a detachment mechanism; the endoclamp (10) comprising a portion of ferromagnetic material; a cylindrically-shaped introduction guide (20) assembled with the detachable surgical endoclamp (10), the introduction guide (20) comprising a mechanism to detach the endoclamp (10); and at least one remote traction component (30) for the endoclamp (10), acting through the application of an electromagnetic field over the ferromagnetic portion of the endoclamp (10).

18 Claims, 6 Drawing Sheets

(56) References Cited

U.S. PATENT DOCUMENTS

| | | | |
|---|---|---|---|
| 5,465,711 A | 11/1995 | Moll et al. | |
| 5,499,986 A * | 3/1996 | Dimarco | 606/104 |
| 5,782,748 A | 7/1998 | Palmer et al. | |
| 5,797,911 A * | 8/1998 | Sherman et al. | 606/270 |
| 5,849,015 A * | 12/1998 | Haywood et al. | 606/99 |
| 6,358,196 B1 | 3/2002 | Rayman | |
| 6,440,133 B1 * | 8/2002 | Beale et al. | 606/86 A |
| 6,656,199 B1 | 12/2003 | Lafontaine | |
| 6,689,119 B1 | 2/2004 | Di Caprio et al. | |
| 6,916,314 B2 | 7/2005 | Schneider et al. | |
| 7,017,584 B2 | 3/2006 | Garibaldi et al. | |
| 7,169,104 B2 | 1/2007 | Ueda et al. | |
| 7,341,063 B2 | 3/2008 | Garbibaldi et al. | |
| 7,429,259 B2 | 9/2008 | Cadeddu et al. | |
| 7,431,726 B2 | 10/2008 | Spence et al. | |
| 7,691,103 B2 | 4/2010 | Fernandez et al. | |
| 7,799,050 B2 | 9/2010 | Hensley et al. | |
| 8,133,254 B2 | 3/2012 | Dumbauld et al. | |
| 8,480,668 B2 | 7/2013 | Fernandez et al. | |
| 2003/0114731 A1 | 6/2003 | Cadeddu et al. | |
| 2004/0050395 A1 | 3/2004 | Ueda et al. | |
| 2005/0165449 A1 | 7/2005 | Cadeddu et al. | |
| 2006/0293566 A1 | 12/2006 | Brown | |
| 2007/0027458 A1 | 2/2007 | Sixto, Jr. et al. | |
| 2007/0043359 A1 * | 2/2007 | Altarac et al. | 606/61 |
| 2007/0135678 A1 | 6/2007 | Suzuki | |
| 2007/0255273 A1 | 11/2007 | Fernandez et al. | |
| 2008/0243106 A1 | 10/2008 | Coe et al. | |
| 2008/0269779 A1 | 10/2008 | Cadeddu et al. | |
| 2009/0043246 A1 | 2/2009 | Dominguez | |
| 2009/0192344 A1 | 7/2009 | Bakos et al. | |
| 2009/0267717 A1 | 10/2009 | Baskett | |
| 2010/0105984 A1 | 4/2010 | Brewer et al. | |
| 2010/0114126 A1 | 5/2010 | Neff | |
| 2010/0160739 A1 | 6/2010 | Van Lue | |
| 2010/0217245 A1 | 8/2010 | Prescott | |
| 2010/0298645 A1 | 11/2010 | Deutch | |
| 2011/0087223 A1 | 4/2011 | Spivey | |
| 2011/0087224 A1 | 4/2011 | Cadeddu et al. | |
| 2011/0087249 A1 | 4/2011 | Rodrigues et al. | |
| 2011/0283822 A1 | 11/2011 | Cadeddu et al. | |
| 2011/0284014 A1 | 11/2011 | Cadeddu et al. | |
| 2011/0285488 A1 | 11/2011 | Scott et al. | |
| 2011/0313415 A1 | 12/2011 | Fernandez et al. | |
| 2012/0035416 A1 | 2/2012 | Fernandez et al. | |
| 2012/0085358 A1 | 4/2012 | Cadeddu et al. | |
| 2013/0158523 A1 | 6/2013 | Bergs et al. | |
| 2013/0158659 A1 | 6/2013 | Bergs et al. | |
| 2013/0158660 A1 | 6/2013 | Bergs et al. | |

FOREIGN PATENT DOCUMENTS

| | | |
|---|---|---|
| CN | 201079412 Y | 7/2008 |
| DE | 42 12 430 A1 | 10/1993 |
| DE | 10 2005 006 705 A1 | 8/2006 |
| EP | 1 797 823 | 6/2007 |
| WO | WO 2008/131128 | 10/2008 |
| WO | WO 2009/019288 | 2/2009 |
| WO | WO 2009/070743 | 6/2009 |
| WO | WO 2011/091483 A1 | 4/2011 |

OTHER PUBLICATIONS

Dominguez. "Colecistectomia con un trocar asistida por imanes de neodimio. Reporte de un caso." *Asociacion Mexicana de Cirugia Endo.* vol. 8. No. 4. 2007. pp. 172-176.

* cited by examiner

PREVIOUS ART

REMOTE TRACTION AND GUIDANCE SYSTEM FOR MINI-INVASIVE SURGERY

This application is a National Stage Application of PCT/IB2009/054307, filed 1 Oct. 2009, which claims benefit of Serial No. 279-2009, filed 6 Feb. 2009 in Chile and which application(s) are incorporated herein by reference. To the extent appropriate, a claim of priority is made to each of the above disclosed applications.

FIELD OF THE INVENTION

The present invention is directed to a guide and remote traction system for mini-invasive surgery or endocavitary surgery, said system being easily maneuvered, positioned, hooked and used, which diminishes the number of required incisions to perform surgical procedures. In particular, the present invention consists in a guide and remote traction system for mini-invasive surgery or endocavitary surgery that is easily positioned and hooked, comprising: a detachable surgical endoclamp; a detachable and self-closing introduction guide assembled together with said surgical endoclamp; and remote magnetic traction means for said endoclamp.

BACKGROUND OF THE INVENTION

Surgery is under constant change and development. Currently, surgical procedures and technologies are oriented to carry out surgeries that cause the lowest possible injury to the patient. The applied concept is to achieve advantages for the individual, such as lower pain, lower post-surgery recovery periods, shortened hospitalization, lower complications associated to the procedure and better cosmetic results, which results in a better life quality for the patient and savings for health insurance systems. With this inspiration, endoscopic or minimally invasive surgery has been developed, which allows carrying out surgical interventions through small incisions in the patient, hence avoiding larger incisions and the higher metabolic costs of open surgery.

A solution to this need is disclosed in U.S. Pat. No. 7,169,104, published on Mar. 18, 2004, which discloses a remote guide anchoring system including an hooking device that is hooked to a body part in a patient's body; a magnetic clamp made of a magnetic material that is connected to the hooking device; and a magnetic device located outside of the patient's body to guide the clamp, which produces a magnetic field to move said magnetic clamp. As can be seen in this document and its figures, the invention in this document requires a second clamp to close the magnetic clamp or to hook the clamp to the anchoring system. The former solution refers to a solution for digestive endoscopy that is very difficult to apply in laparoscopic surgery since the assembly solution for the clamp and its traction system is very difficult to carry out inside cavities.

Technical Problem

These surgery techniques need entrance points into the individual, which requires performing a total wall incision and generally inserting a working trocar (or port). Through these entrances, necessary elements are introduced, both optical (cameras for internal visualization) and surgical tools, e.g. clamps, electroscalpel, scissors, etc. In this type of surgery, it is necessary to detach and raise adjacent organs or tissues for a cleaner and more effective surgery result. Usually, this detachment and rising is performed by using clamps or hooking means, which are directly manipulated from the outside through a working port.

These working ports are the incision points that must be performed in the body wall of the individual, with the risks and complications associated to a total thickness body wall incision, mainly: important post-surgery pain, intra- and post-surgery bleeding risk, infection risk and risk of developing subsequent hernias. All these complications decrease the life quality of the patient and increase health insurance costs. Additionally, there is also an important aesthetical issue, since these incisions necessarily leave a subsequent scar as a sequel. Due to this, it is necessary to use the minimal possible number of incisions to perform the desired surgical procedure, therefore decreasing intra- and post-surgery complications and hence getting the best post-surgery results.

Solution to Problem

The present invention solves the problem of positioning and effectively hooking an endoclamp to an organ or tissue to be pulled, making the assembly easy to use, since it comprises a self-closing endoclamp actuated from the introduction guide. Subsequently, this endoclamp is moved by applying a magnetic force through the body wall using the remote traction means.

Advantageous Effects of Invention

The present invention has been realized, consisting in a guide and remote traction system for mini-invasive surgery with easy positioning and hooking and lower injury since it makes possible to eliminate one or several incisions performed with the previous art techniques, which brings about a benefit for patients. This allows a significant reduction on the recovery time of patients, removing potential risks associated to incisions and avoiding undesirable scars. Furthermore, the present invention proposes a guide and remote traction system comprising a hooking mechanism to the organ or tissue to be treated that is easily and safely operated, which facilitates its use by physicians. Therefore, the present invention is beneficial, since it decreases the number of incisions to perform the surgery and is easily used. The present invention solves a problem of positioning and effective hooking to the organ to be pulled, allowing an easy use and performing surgery with lower injury to the patient.

PREFERRED EMBODIMENT OF THE INVENTION

The present invention consists in a guide and remote traction system for mini-invasive surgery in a body cavity that is easily positioned and hooked and causes lower injury, comprising:

at least one endoclamp with surgical hooking means, assembled with a guide and at an initially open position; and at a naturally closed position when detached from said guide by the detachment mechanism; said endoclamp comprising a portion of ferromagnetic material at the end opposed to said hooking means;

a cylindrically-shaped introduction guide assembled with said detachable surgical endoclamp, said guide comprising a mechanism to detach said endoclamp;

at least one remote traction means for said at least one endoclamp, acting through the application of an electromagnetic field over the ferromagnetic portion of said endoclamp from outside of said body cavity.

Figure 1:
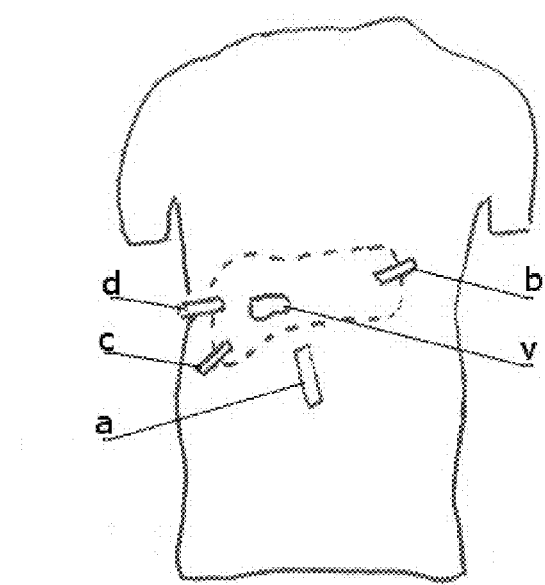
FIG. 1 is a schematic view of a mini-invasive surgery, particularly a laparoscopic cholecystectomy, according to the previous art.

As observed in FIG. 1, a mini-invasive laparoscopic-like surgery is performed by techniques of the prior art in which, in this case, 4 incisions are practiced in the abdominal wall to place the trocars, wherein 1 trocar (a) is used for insertion of an endoscopic camera, and 3 trocars (b, c and d) are used to rise, manipulate and section the organ to be treated, e.g. the gall bladder (v), with hooking means such as conventional laparoscopic clamps.

Figure 2:
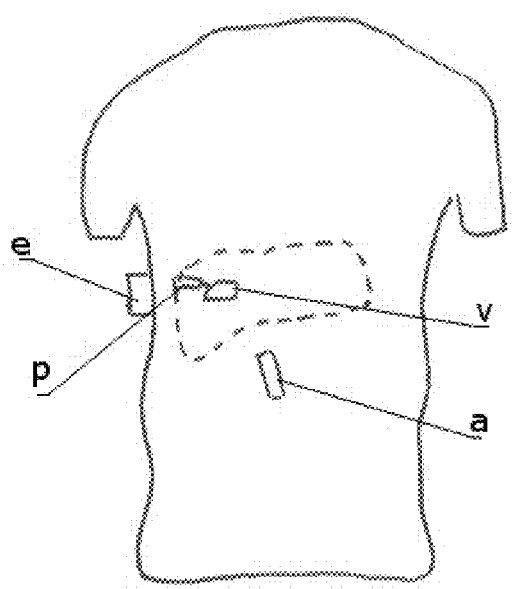
FIG. 2 is a schematic view of a mini-invasive surgery with the guide system with remote traction according to the present invention. A decrease in the number of access points can be observed.

Instead, FIG. 2 shows a mini-invasive surgery using the guide system and remote traction according to the present invention; wherein it can be appreciated that only one incision is carried out in the abdominal wall for only one trocar (a), through which one or more clamps (p) are introduced, which are driven by one or more magnets or electromagnets (e) to manipulate the organ (v); the endoscopic camera to visualize the mini-invasive surgery is introduced through this same trocar, as well as an element to dissect and subsequently extract the tissue or organ.

Figure 3:
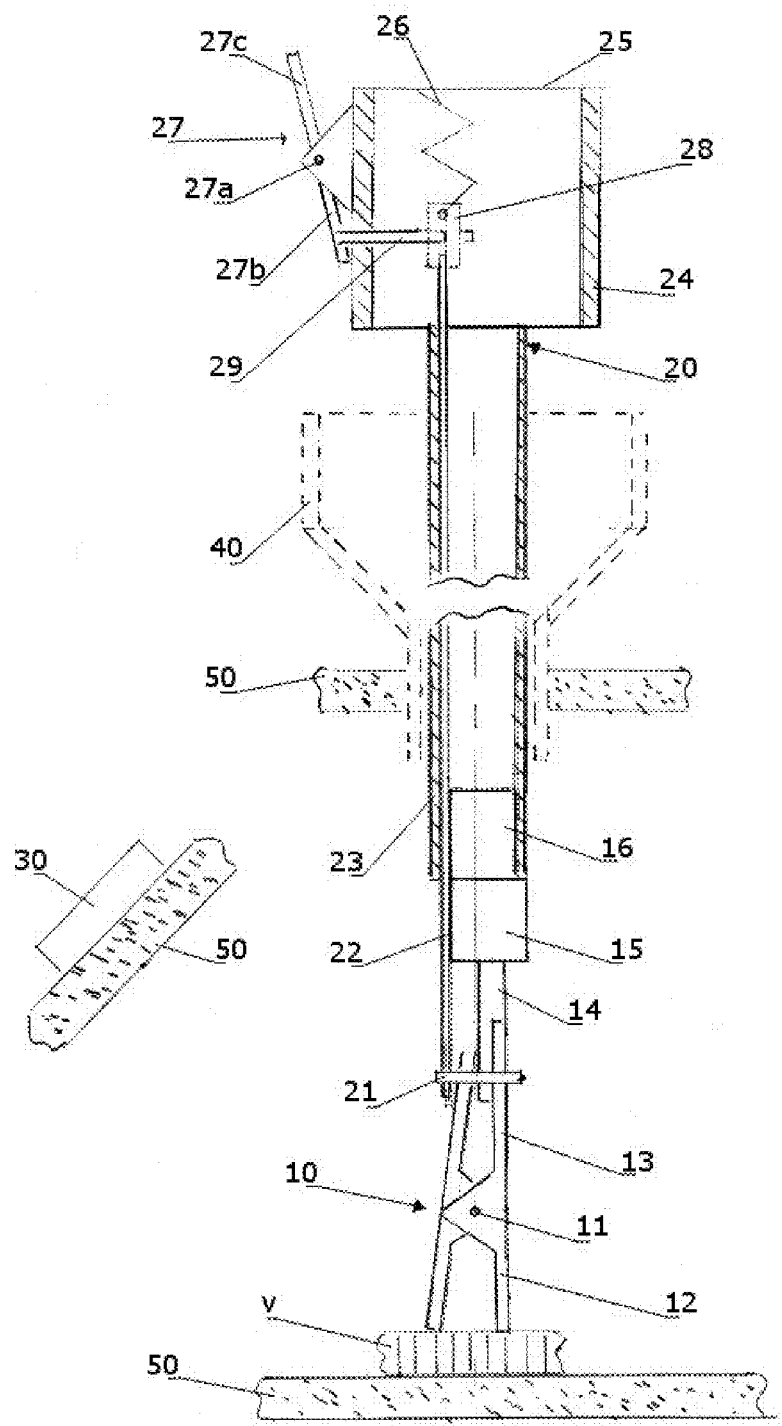
FIG. 3 is a schematic view of the guide system and remote traction according to the present invention in an initial configuration comprising an introduction guide and an assembled open clamp.

As illustrated in FIG. 3, the guide and remote traction system for mini-invasive surgery in a body cavity that is easily positioned and hooked and causes lower injury, comprises: an introduction guide (20) assembled with a detachable surgical endoclamp (10) and a remote traction means (30) of said endoclamp (10) to move said endoclamp by applying a magnetic field over an end of said clamp from the outside of said body cavity, e.g. an electromagnet.

Said endoclamp (10) comprises two separate pieces substantially at its center and rotatable about an axis (11), each of said separate pieces defining a hooking end (12) and a handling end (13) with a radial spring (not shown in the Figures) that holds the endoclamp (10) in its naturally closed position. A first handling end (13) is joined to a projection (14) coupled to a cylindrical butt means (15) with a diameter wider than projection (14), and said butt means (15) extends to an anchoring means (16) introduced inside the guide (20); wherein the butt means (15) and anchoring means (16) comprise a portion made of a ferromagnetic material, e.g. iron, nickel, cobalt, iron oxides, etc.

Said detachment mechanism of said introduction guide (20) comprises a securing ring (21) joined to a first end of a substantially rod-like connecting piece (22), said connecting piece (22) passing through the inside of a guide tube (23), said guide tube (23) connecting at one end to the anchoring means (16) of the endoclamp (10) and at the other end to a detaching set (24) to detach said endoclamp (10); said connection piece (22) is joined at its second end to an unlocking piece (28) connected to a tensioned spring (26) fixed to the rear wall (25) of the detaching set (24); said unlocking piece (28) having a perforation with a pin (29) passing therethrough. Said pin (29) is fixed at its end to an actuator (27) that is rotatable around a central axis (27*a*) that defines an operative end (27*b*) and an actuator end (27*c*).

In an initial position, said rotatable actuator (27) is in a first position with the operative end (27*b*) closer to the unlocking set (24) than the actuator end (27*c*), which is far away from the unlocking set (24); the pin (29) passes through the perforation of the unlocking piece (28) and the unlocking piece is located at a distance from the rear wall (25) longer than the natural spring length (26) in such a way as to hold the spring in tension in its first position. In this initial position, the connecting piece (22) holds the securing ring (21) around and joining the handling ends (13) in such a way as to hold the endoclamp (10) open, i.e. with separated hooking ends (12).

Figure 4:
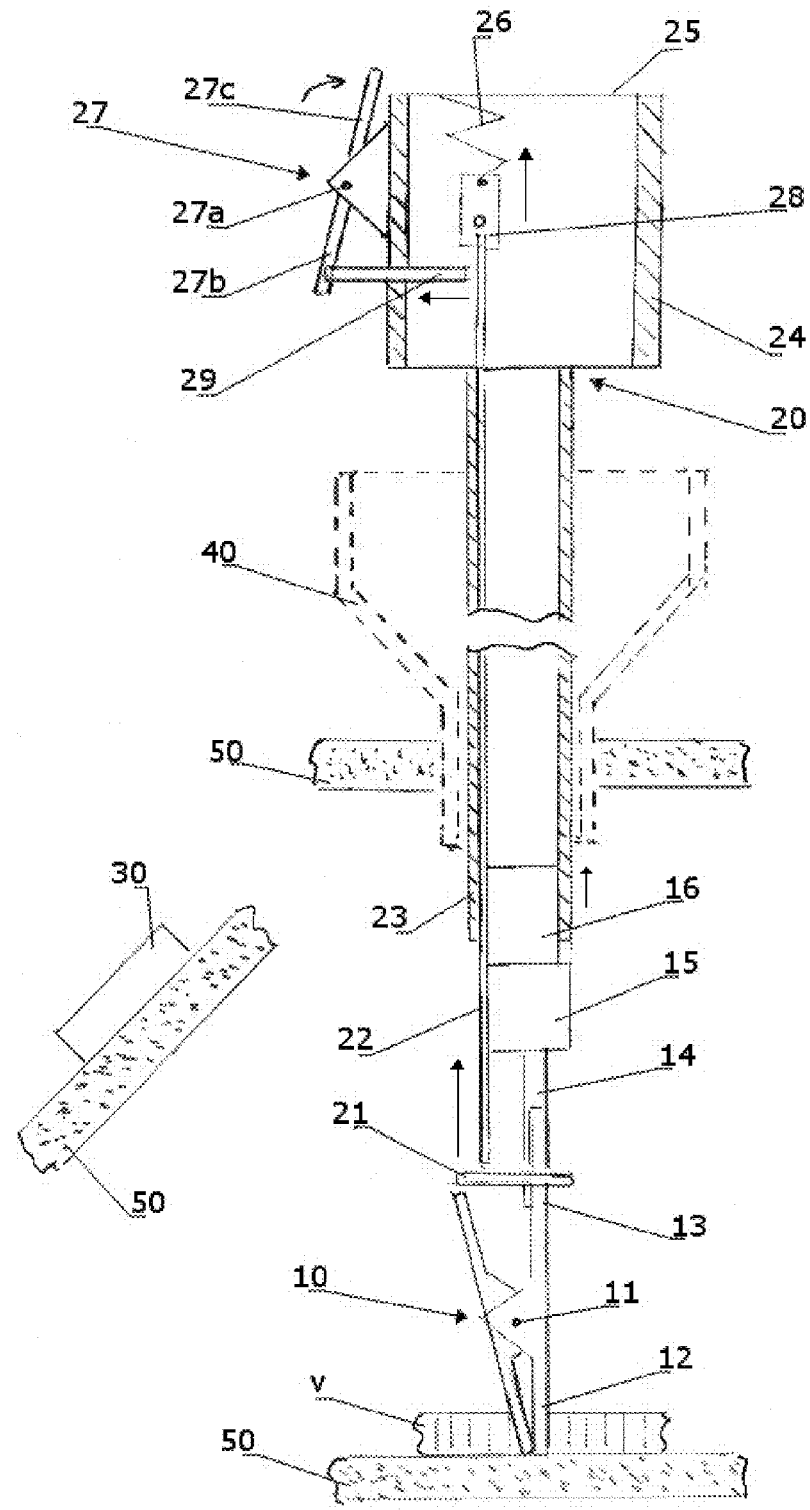
FIG. 4 is another schematic view of the guide system and remote traction according to the present invention in a detachment position with a closed clamp.

When introducing the introduction guide (20) assembled with the endoclamp (10) through a trocar installed in a body cavity subjected to mini-invasive surgery, the introduction guide (20) and the endoclamp (10) can be guided, introduced and alignedly actuated through said trocar. When the endoclamp (10) is in its initial position, the endoclamp is open and is directed toward the organ or tissue (v) to be treated. When the endoclamp (10) is correctly placed at the organ or tissue (v), the endoclamp is put into a, unlock position, shown in FIG. 4, which is achieved by pressing the actuator end (27*c*) as to remove the pin (29) from the perforation of the unlocking piece (28); in this way, the restriction imposed on the spring (26) is released and the spring returns to its natural position, bringing together the unlocking piece (28) and the rear wall (25), and removing the securing ring (21) from the endoclamp (10) by means of the connection piece (22). In turn, the endoclamp (10) is released into its natural position, and the hooking ends (12) are closed, thus trapping the organ or tissue (v).

Figure 5:
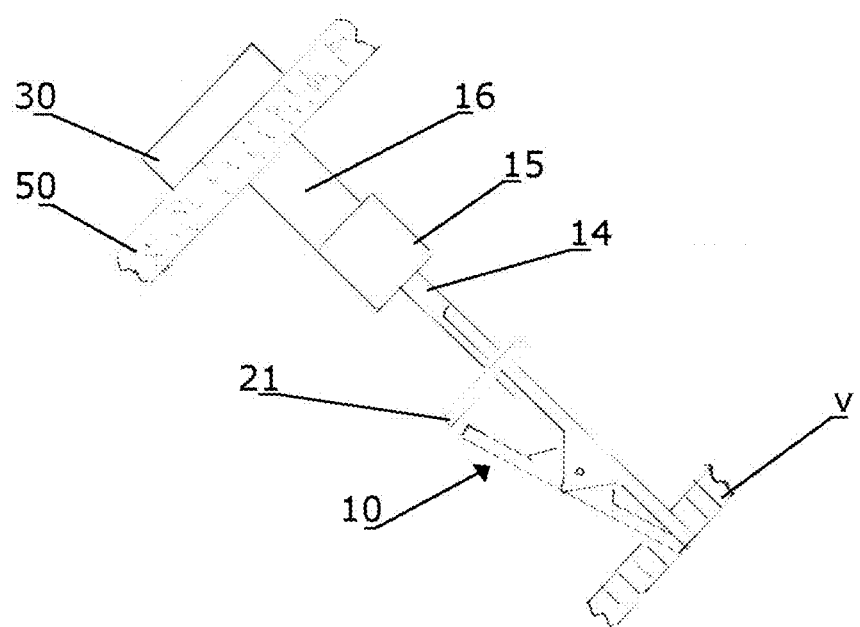
FIG. 5 is a schematic view of the endoclamp detached from the introduction guide in traction operative position.

As shown in FIG. 5, when the endoclamp (10) is fixed to the organ or tissue (v), the introduction guide (20) is removed from the trocar and it can be used to introduce another element into the body cavity; furthermore, the endoclamp (10) is brought close to the body cavity wall (50) near the remote traction means (30) and the magnetic field is activated in such a way as to make said endoclamp (10) to be attracted by said remote traction means (30) and orienting its butt means (15) and the hooking means (16) toward the inner side of the body cavity wall (50). In this way, the remote traction means (30) can guide and position the endoclamp (10) remotely from the outside of the body cavity.

Then, in the aforementioned way, an organ or tissue in a body cavity can be manipulated with one or more endoclamps by repeating the described procedure. The organ remains located in an optimal position to carry out the corresponding surgical intervention with only one incision to install a single trocar.

Said one or more endoclamps remain fixed at their position or can be moved along the body cavity, thanks to one or several remote traction means of said endoclamp by applying an electromagnetic field over the ferromagnetic portion of said endoclamp from the outside of said body cavity.

Preferably, said remote traction means generates an electromagnetic field with a magnetic induction ranging from 0.1 to 1 Tesla (1,000 to 10,000 Gauss) in the surroundings of said traction means, to generate a force ranging from 2.94 to 4.9 N (300 and 500 grams) over the endoclamp according to the present invention at a distance ranging from 10 to 30 mm of the abdominal wall; reaching a body wall width of up to 80 mm in case of obesity. For this end, said remote traction means comprises a permanent magnet such as, e.g. a magnetized steel or Alnico (alloy comprising 24% by weight of cobalt, 8% by weight of aluminum, 14% by weight of nickel, 51% by weight of iron and 3% by weight of copper) or ferrite (80% by weight of iron oxide and 20% by weight of strontium oxide) magnet.

More preferably, said traction means comprises a rare earth mineral magnet, e.g.: $RE-M_5$- and $RE_2M_{17}$-type, wherein "RE" is samarium (Sm), promethium (Pr) and neodymium (Nd) and "M" is a mixture of cobalt (Co) with metals such as iron (Fe), copper (Cu), zirconium (Zr), titanium (Ti), hafnium (Hf) and manganese (Mn); e.g. $SmCo_5$ made by GE Research Lab in Schenectady, Nueva York (EEUU), or "neodymium-iron-boron", $Nd_2Fe_{14}B$, developed in 1983 by Sumitomo (Japan) and General Motors (EEUU).

EMBODIMENT OF THE INVENTION

According to another preferred embodiment of the invention, said remote traction means can comprise an electromagnet and a voltage regulator to vary the magnetic induction generated by varying the voltage on the electromagnet. Preferably, said electromagnet generates an electromagnetic field with a magnetic induction ranging from 0.1 to 1 Tesla (1,000 to 10,000 Gauss) in the surroundings of said traction means, to generate the required force over the endoclamp according to the present invention at a distance ranging from 10 to 30 mm.

According to another preferred embodiment of the invention, said remote traction means can comprise an electromagnet and an electric current regulator to vary the generated magnetic induction by varying the electric current intensity over the electromagnet, said magnetic induction ranging from 0.1 to 1 Tesla (1,000 to 10,000 Gauss) according to the present invention.

According to an embodiment of the present invention, said electromagnet can comprise a paramagnetic material core that comprises one or several of the following materials: air, aluminum, magnesium, titanium, ferric chloride and tungsten.

According to another embodiment of the present invention, said electromagnet can comprise a ferromagnetic material core that comprises one or several of the following materials: iron, nickel, cobalt, aluminum, iron-silicon or alnico and permalloy alloys, this latter comprising 20% by weight of steel and 80% by weight of nickel.

Figure 6:
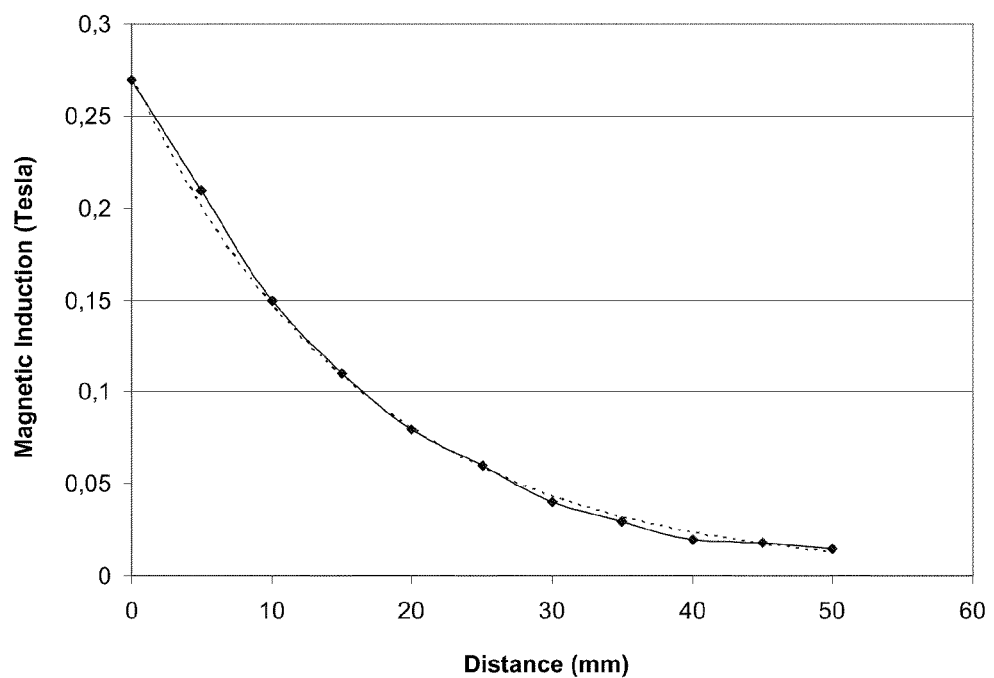
FIG. 6 shows a plot of magnetic field density as a function of distance generated by a remote traction means according to the present invention.
Figure 7:
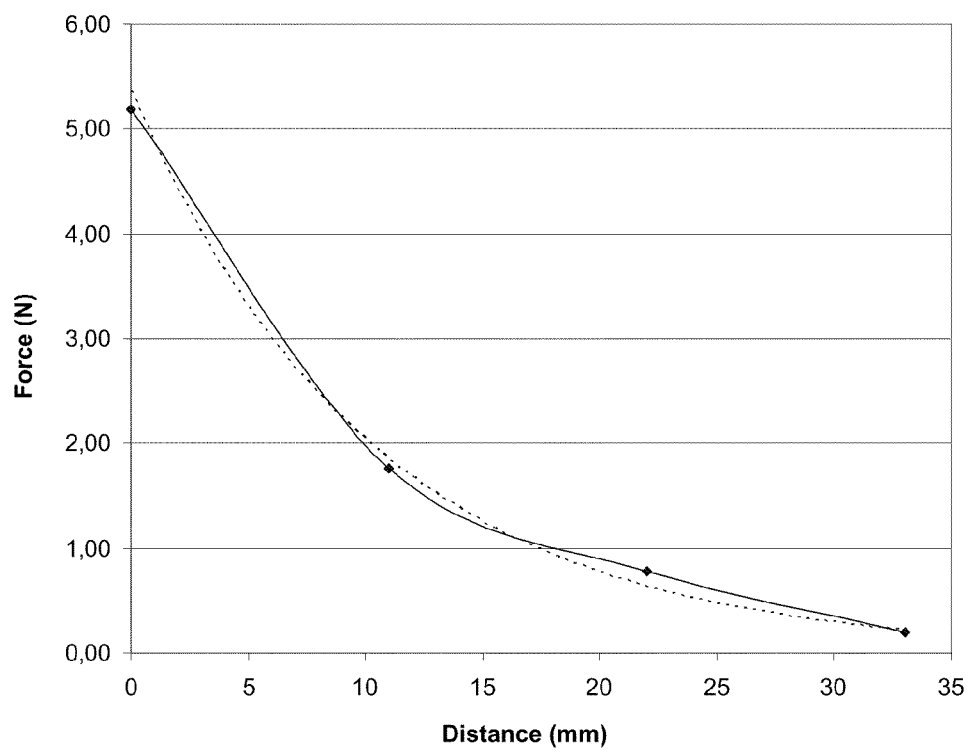
FIG. 7 shows a plot of magnetic field force as a function of distance generated by said remote traction means over an endoclamp according to the present invention.

In a first example of the present invention, FIG. 6 shows a plot of magnetic field density as a function of distance generated by a remote traction means according to the present invention which comprises a rare earth magnet. FIG. 7 shows a plot of magnetic field force as a function of distance generated by said remote traction means over an endoclamp according to the present invention. From FIG. 7, a characteristic magnet curve can be interpolated using equation: (a) $F=5.3757e^{-0.0967d}$; with a quadratic fit with $R^2=0.9897$, being F the force (in N) generated over the endoclamp and d the distance (in mm) between the remote traction means and the endoclamp; a magnet with these characteristics can generate 1.76 N (180 grams) at a distance of 11 mm according to the width requirements of the body cavity and the organ to be manipulated with the endoclamp of this first example.

According to the thickness of the patient's body cavity and the weight of the organ to be manipulated, in a second example a 2.94 N (300 grams) can be required to maintain and manipulate an organ through a body cavity of 20 mm. Thanks to FIG. 7 and equation (a), a new characteristic curve can be easily interpolated: $2.94=5.3757e^{-0.0967*20}+B$; therefore $B=2.1628$; and the resulting equation is: (b) $F=5.3757e^{-0.0967*d}+2.1628$; wherein for a 0 mm distance, said magnet must generate a force of 7.5385 N (739 grams) over said endoclamp.

Figure 8:
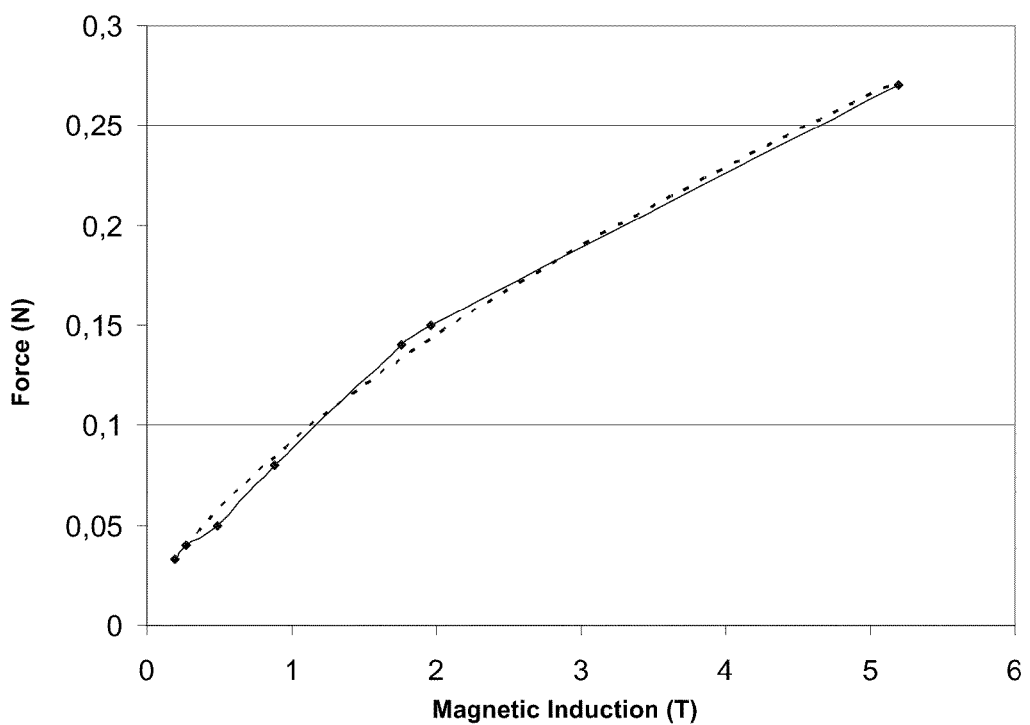
FIG. 8 shows a plot relating the magnetic induction of a traction means with a rare earth magnet with the force generated over an endoclamp by said magnetic induction, said traction means and said endoclamp according to the present invention.

FIG. 8 shows a plot relating the magnetic induction of a rare earth magnet with the force generated over the endoclamp according to the present invention, with the equation: (c) $B=0.0917*F^{0.66}$; with a quadratic fit with $R^2=0.9915$, wherein F is the force in Newtons and B is the magnetic induction in Teslas; for this second example, the magnet required for the remote traction means according to the present invention should be dimensioned for a magnetic induction of 0.3478 Teslas (3478 Gauss).

Figure 9:
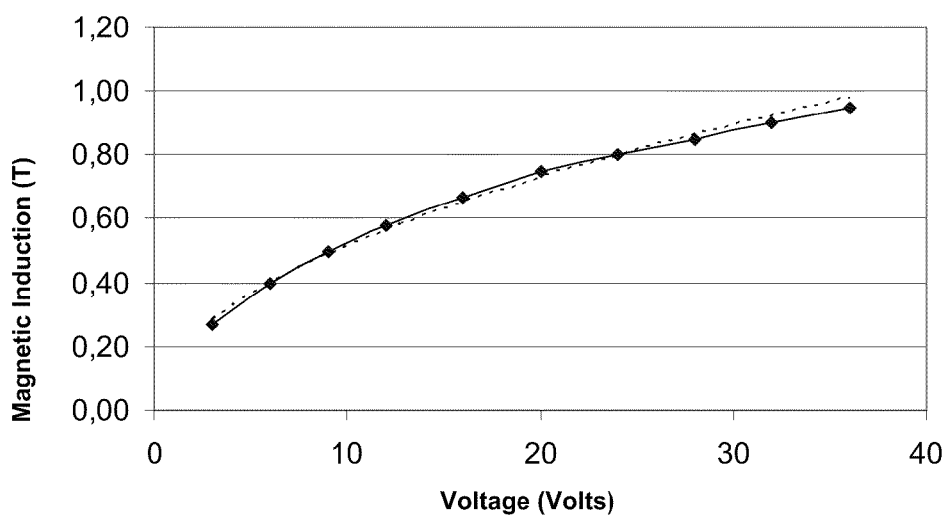
FIG. 9 shows a plot of magnetic induction as a function of voltage over an electromagnet of a traction means according to the present invention.

According to another preferred embodiment of the invention, said remote traction means can comprise an electromagnet and a voltage regulator to vary the magnetic induction generated by varying the voltage on the electromagnet. FIG. 9 shows a plot of magnetic induction as a function of voltage over an electromagnet with a 2 A current I; a path length of 8.3 cm; a spire number of 4.245; and a cold-laminated steel core with a diameter of 10 mm and permeability 1.99. Said plot of FIG. 9 allows obtaining a characteristic electromagnet curve represented by equation: (d) $B=0.1621*V^{0.5018}$; with a quadratic fit having $R^2=0.9956$, wherein B is the magnetic induction in Teslas at a distance of 0 mm from the electromagnet and V is the voltage in Volts applied over said electromagnet.

For the aforementioned example, where a 2.94 N (300 grams) force must be generated over the endoclamp according to the present invention through a body wall of 20 mm, a magnetic induction of 0.3478 Teslas (3478 Gauss) should be produced at a distance of 0 mm; therefore, according to the plot in FIG. 9 and using equation (d), the required voltage is $V=(0.3478/0.1621)^{1/0.5018}=4.58$ Volts. Hence, the voltage regulator of said traction means must be regulated to get the deduced 4.58 Volts voltage. In this way, the traction means that comprises an electromagnet with a voltage regulator or a current regulator can be adjusted to apply the minimal necessary force over the endoclamp to hold it firmly at its position against the body cavity without applying an excessive force that could damage the tissues and other organs of the body cavity under surgery.

INDUSTRIAL APPLICABILITY

The present invention has industrial applicability in the manufacturing industry of mini-invasive surgery or endocavitary surgery tools. The present invention is especially useful in videolaparoscopic cholecystectomy, but is not limited to this procedure.

The invention claimed is:

1. An apparatus, comprising:
a surgical device;
a shaft having a proximal end portion and a distal end portion and configured to be removably coupled to the surgical device having an anchor portion and an attachment portion, the shaft defining a volume configured to receive the anchor portion when the distal end portion is coupled to the surgical device, an attachment portion of the surgical device being disposed outside of the volume when the anchor portion is disposed within the volume, the surgical device including a retention member configured to retain the attachment portion in a first configuration;
a coupling member movably disposed within the shaft, a distal end portion of the coupling member configured to move the retention member when the coupling member is moved from a first position to a second position, thereby initiating movement of the attachment portion from the first configuration to a second configuration, the coupling member configured to be disposed between a side wall of the shaft and the anchor portion of the surgical device and in contact with the anchor portion when the coupling member is in the first position, the anchor portion being released from the distal end portion of the shaft when the coupling member is moved from the first position to the second position; and
an actuator assembly coupled to the proximal end portion of the shaft, the actuator assembly configured to move the coupling member from the first position to the second position.

2. The apparatus of claim 1, wherein the coupling member is configured to move substantially irreversibly the retention member when the coupling member is moved from the first position to the second position.

3. The apparatus of claim 1, wherein the coupling member is configured to move proximally within the shaft from the first position to the second position.

4. The apparatus of claim 1, wherein:
the coupling member is configured to move substantially parallel to a longitudinal axis of the shaft from the first position to the second position; and
the actuator assembly includes an actuator member operably coupled to the coupling member, the actuator member configured to be moved substantially normal to the longitudinal axis of the shaft to initiate movement of the coupling member.

5. The apparatus of claim 1, wherein the actuator assembly includes a biasing member configured to urge the coupling member towards the second position.

6. The apparatus of claim 1, wherein the actuator assembly includes a retention pin and a biasing member, the retention pin operably coupled to a proximal end portion of the coupling member to retain the coupling member in the first position, the biasing member configured to urge the coupling member towards the second position, the actuator assembly configured to decouple the retention pin from the proximal end portion of the coupling member when actuated.

7. The apparatus of claim 6, wherein the actuator assembly includes an actuator member configured to move the retention pin in a direction substantially normal to a longitudinal axis of the coupling member when the actuator member is actuated.

8. The apparatus of claim 1, wherein the attachment portion is moved from the first configuration to the second configuration and the anchor portion is released from the distal end portion of the shaft in a substantially continuous operation when the actuator assembly is actuated.

9. The apparatus of claim 1, wherein the surgical device is a clamp and the anchor portion of the clamp is constructed from a ferromagnetic material.

10. An apparatus, comprising:
a surgical device;
a shaft having a distal end portion configured to be removably coupled to the surgical device having an anchor portion and an attachment portion, the shaft defining a volume configured to receive the anchor portion when the distal end portion is coupled to the surgical device, and the attachment portion comprising a clamp having a first piece rotatably connected to a second piece;
a coupling member configured to move from a first position to a second position within the shaft in a direction substantially parallel to a longitudinal axis of the shaft, a distal end portion the coupling member configured to initiate movement of the attachment portion of the surgical device from a first configuration to a second configuration when the coupling member is moved from the first position to the second position; and
an actuator assembly coupled to a proximal end portion of the shaft, the actuator assembly including an actuator member operably coupled to the coupling member, the actuator member configured to be moved substantially normal to the longitudinal axis of the shaft to initiate movement of the coupling member from the first position to the second position.

11. The apparatus of claim 10, wherein the coupling member is configured to at least partially retain the anchor portion of the surgical device within the volume defined by the shaft when the coupling member is in the first position.

12. The apparatus of claim 10, wherein the attachment portion is moved from the first configuration to the second configuration and the anchor portion is released from the distal end portion of the shaft in a substantially continuous operation when the actuator assembly is actuated.

13. The apparatus of claim 10, wherein the actuator assembly includes a biasing member configured to urge the coupling member towards the second position.

14. The apparatus of claim 10, wherein the actuator assembly includes a retention pin and a biasing member, the retention pin operably coupled to a proximal end portion of the coupling member to retain the coupling member in the first position, the biasing member configured to urge the coupling member towards the second position, the actuator assembly configured to decouple the retention pin from the proximal end portion of the coupling member when actuated.

15. An apparatus, comprising:
a surgical device;
a shaft having a distal end portion configured to be removably coupled to the surgical device having an anchor portion and an attachment portion, the shaft defining a volume configured to receive the anchor portion when the distal end portion is coupled to the surgical device, and the attachment portion comprising a clamp having a first piece rotatably connected to a second piece;
a coupling member configured to move from a first position to a second position within the shaft in a direction substantially parallel to a longitudinal axis of the shaft, a distal end portion the coupling member configured to initiate movement of the attachment portion of the surgical device from a first configuration to a second configuration when the coupling member is moved from the first position to the second position, the coupling member is configured to at least partially retain the anchor portion of the surgical device within the volume defined by the shaft when the coupling member is in the first position; and an actuator assembly coupled to a proximal end portion of the shaft, the actuator assembly configured to move the coupling member from the first position to the second position, the coupling member and the actuator assembly collectively configured such that the attachment portion is moved from the first configuration to the second configuration and the anchor portion is released from the distal end portion of the shaft in a substantially continuous operation when the actuator assembly is actuated.

16. The apparatus of claim 15, wherein:

the coupling member is configured to move substantially parallel to a longitudinal axis of the shaft from the first position to the second position; and the actuator assembly includes an actuator member operably coupled to the coupling member, the actuator member configured to be moved substantially normal to the longitudinal axis of the shaft to initiate movement of the coupling member.

17. The apparatus of claim 15, wherein the actuator assembly includes a biasing member configured to urge the coupling member towards the second position.

18. The apparatus of claim 15, wherein the actuator assembly includes a retention pin and a biasing member, the retention pin operably coupled to a proximal end portion of the coupling member to retain the coupling member in the first position, the biasing member configured to urge the coupling member towards the second position, the actuator assembly configured to decouple the retention pin from the proximal end portion of the coupling member when actuated.

* * * * *